United States Patent [19]

Peters

[11] Patent Number: 4,587,374
[45] Date of Patent: May 6, 1986

[54] OLEFIN ISOMERIZATION PROCESS
[75] Inventor: Bruce C. Peters, Baton Rouge, La.
[73] Assignee: Ethyl Corporation, Richmond, Va.
[21] Appl. No.: 715,824
[22] Filed: Mar. 25, 1985

Related U.S. Application Data

[63] Continuation-in-part of Ser. No. 592,536, Mar. 26, 1984, abandoned.
[51] Int. Cl.$^4$ .......................... C07C 5/25; C07C 5/22; C07C 5/13
[52] U.S. Cl. .................................. 585/670; 585/665; 585/671; 585/654
[58] Field of Search ................ 585/670, 671, 665, 664

[56] References Cited

U.S. PATENT DOCUMENTS 3,398,205 8/1968 Chappell et al. .................... 585/377

OTHER PUBLICATIONS

CRC Press, Handbook of Chemistry and Physics, "Value of Chemical Thermodynamic Property of Hydrocarbons," 57th Edition, p. D-83, 1976–1977.

*Primary Examiner*—John Doll
*Assistant Examiner*—Chung K. Pak
*Attorney, Agent, or Firm*—Donald L. Johnson; John F. Sieberth; Joseph D. Odenweller

[57] ABSTRACT

Vinylidene olefins which contain the olefinic unit

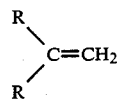

are isomerized in high yield to form di-substituted internal olefins containing the olefinic unit —CH=CH— by heating to 150°–350° C. in contact with an iron carbonyl catalyst. Only minor amounts of tri-substituted internal olefins which contain the olefinic unit

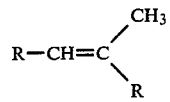

are formed.

6 Claims, No Drawings

OLEFIN ISOMERIZATION PROCESS

This application is a continuation-in-part of application Ser. No. 592,536 filed Mar. 26, 1984 now abandoned.

BACKGROUND OF THE INVENTION

Mixtures of terminal olefins, commonly referred to as α-olefins, are made commercially by ethylene chain growth of aluminum alkyls followed by displacement. Such products are mainly α-olefins having the structure:

$$R-CH_2-CH=CH_2$$

wherein R is an aliphatic hydrocarbon group. These are referred to as "vinyl olefins". A substantial portion of the α-olefins can be in the form of "vinylidene olefins" which have the structure:

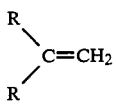

wherein both R groups are aliphatic hydrocarbon groups.

For many uses it is highly desirable to retain the olefin unsaturation in the terminal position. However, in making alkyl sulfonate surfactants by the known process of reacting an olefin with hydrogen sulfide in the presence of a Lewis Acid catalyst followed by oxidation with for example nitric oxide and oxygen to form sulfonic acid, it has been found that superior surfactant properties are achieved using internal olefins. Internal olefins can be made from α-olefins by isomerizing the olefin double bond from a terminal to an internal position. When this is done, using conventional isomerization catalyst such as alumina or silica/alumina, a major portion of the olefin groups of the vinylidene olefins are isomerized to the adjacent carbon-carbon bond forming what is termed "tri-substituted" internal olefins which have the structure:

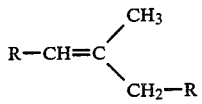

wherein each R is an aliphatic hydrocarbon group. Tri-substituted internal olefins are not as effective when converted to sulfonate surfactants as are the "di-substituted" internal olefins in which the olefin has the structure:

$$R-CH=CH-R$$

wherein each R is an aliphatic hydrocarbon group. Accordingly, a need exists for an isomerization process that will convert vinylidene olefins to mainly di-substituted internal olefins and minimize formation of tri-substituted internal olefins.

Iron carbonyl has been used to isomerize the double bond on certain olefins. Yardley et al, U.S. Pat. No. 4,338,173 describe the isomerization of an olefin double bond in the presence of iron carbonyl under ultraviolet light. The double bond migrates to the adjacent carbon-carbon bond. If this were applied to vinylidene olefins, one would expect the product to be a tri-substituted olefin.

Casey et al, J. Am. Chem. Soc., 95, Apr. 4, 1973, p. 2248-53, describe the isomerization of 3-ethyl-1-penetene in the presence of tri-iron dodecacarbonyl. The double bond migrates to the adjacent carbon-carbon bond forming 3-ethyl-2-pentene, a tri-substituted internal olefin. Similar results were obtained with 3-methyl-1-butene.

Bingham, et al, J. Chem. Soc., 14, 1974, p. 1521, report the isomerization of pent-1-ene in the presence of an iron carbonyl to form a cis-trans mixture of pent-2-ene. Chappell, et al, U.S. Pat. No. 3,398,205, describe the isomerization of cyclic diene using an iron carbonyl catalyst under carbon monoxide pressure. Kroll, U.S. Pat. No. 3,439,054, teach the use of a complex of iron carbonyl and tri-alkyl aluminum as a hydrogenation and isomerization catalyst. Contrary to what is taught by Chappell, et al, Kroll suggests that carbonyls alone will not isomerize cyclic dienes.

None of the prior art contains disclosure of the isomerization of a vinylidene olefin using an iron carbonyl catalyst and the prior art would predict that the product of such an isomerization if successful would form mainly tri-substituted internal olefins.

SUMMARY OF THE INVENTION

It has now been discovered that the olefinic double bond of vinylidene olefins can be isomerized at elevated temperatures using an iron carbonyl catalyst to form mainly di-substituted olefins rather than tri-substituted olefins which are obtained using conventional isomerization catalyst such as alumina or silica alumina.

DESCRIPTION OF THE PREFERRED EMBODIMENTS

A preferred embodiment of the invention is a process for isomerizing the olefinic double bond of a vinylidene olefin having the structure:

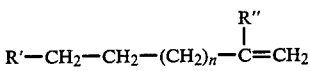

wherein R' and R'' are aliphatic hydrocarbon groups and n is an integer from 0–10 or a mixture of olefins containing a substantial amount of said vinylidene olefin, said process comprising contacting said vinylidene olefin or mixture thereof with a catalytic amount of an iron carbonyl at a temperature of about 150°–350° C. whereby the major isomerization product of said vinylidene olefin is a di-substituted internal olefin having the structure:

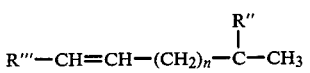

wherein R''' and R'' are aliphatic hydrocarbon groups and n is an integer from 0–10 and only a minor amount of tri-substituted internal olefin.

Examples of vinylidene olefins that can be isomerized to di-substituted olefins are 2-methyl-1-pentene, 2,5-dimethyl-1-hexene, 2,6-dibutyl-1-hexene, 2-octyl-5,5-dimethyl-1-pentcosene and the like.

Preferably, R' and R'' are aliphatic hydrocarbon groups containing 1 to about 30 carbon atoms. More preferably, R' and R" are substantially linear aliphatic hydrocarbon groups containing 1 to about 20 carbon atoms. Still more preferably, R' is a substantially linear aliphatic hydrocarbon group containing 1 to about 20 carbon atoms and R" is a methyl group. Examples of the more preferred vinylidene olefins are 2-propyl-1-pentene, 2-ethyl-1-dodecene, 2-octadecyl-1-dococene and the like.

Examples of the still more preferred vinylidene olefins are 2-methyl-1-pentene, 2-methyl-1-octene, 2-methyl-1-dodecene, 2-methyl-1-tetradecene, 2-methyl-1-hexadecene, 2-methyl-1-octadecene, 2-methyl-1-eicosene and the like.

It has now been found that when using an iron carbonyl catalyst, a majority of the olefinic double bonds migrate at least two bonds down the aliphatic chain to form a di-substituted olefin rather than the expected tri-substituted olefin which would result if the olefinic double bond migrated only one bond down the aliphatic chain. For example in a mixture of $C_{18}$ olefins containing about 37% vinylidene olefins it was found that about 25% of this could be isomerized and that of this isomerized vinylidene olefin 70% formed internal di-substituted olefin and only 30% formed tri-substituted olefin. The reason for this is not clear since the tri-substituted or tert-olefin would be expected to be more stable and thus be the main isomer product as it is with conventional catalysts, such as alumina or silica alumina.

It is not necessary that all of the olefin to be isomerized be vinylidene olefin. The vinylidene olefin may be present in a mixture of olefins such as mixtures containing vinylidene olefins, vinyl olefins and internal olefins. The non-vinylidene olefins are apparently isomerized in a conventional manner to form mixtures of internal olefins.

In the best mode of carrying out the invention, the vinylidene olefins are part of a mixture of olefins obtained by the Ziegler process of triethyl aluminum-ethylene chain growth and displacement. This is a commercially practiced process. A major portion of the olefins are vinyl olefins having the structure:

$$R-CH_2-CH=CH_2$$

wherein R is an aliphatic hydrocarbon group. The R group can contain from 1 to about 50 carbon atoms. More preferably, the R group contains up to about 30 carbon atoms. Examples of these vinyl olefins are 1-butene, 1-hexene, 1-octene, 1-decene, 1-dodecene, 1-tetradecene, 1-hexadecene, 1-octadecene, 1-eicosene, 5-methyl-1-hexadecene, 5-ethyl-1-heptene and the like.

In a highly preferred embodiment R is a substantially linear aliphatic hydrocarbon group containing about 5-23 carbon atoms such as 1-octene, 1-dodecene, 1-hexadecene, 1-octadecene, 1-eicosene, 1-docosene, 1-tetracosene and 1-hexacosene.

The initial olefin mixture prior to isomerization can contain internal olefins. In the preferred embodiment, the amount of internal olefin in the initial mixture is quire low. Amounts of 0 up to about 15 wt% can be encountered. Generally the amount of initial internal olefin is about 3-10 wt% of the olefin mixture. Of course, this is exclusive of any internal olefin which might be added to the initial olefin mixture and hence the amount of internal olefins in the isomerization feed is not a critical limitation.

When the olefin mixture is made by the known commercial process using triethyl aluminum-ethylene chain growth and displacement, the resultant olefin mixture will contain about 50-95 wt% vinyl olefins and 5-50 wt% vinylidene olefins and 0 up to about 15 wt% internal olefins. The total olefins add up to 100% exclusive of non-olefins. In most production, the olefin mixture contains about 1-10 wt% internal olefins of which very little or none is tri-substituted olefins.

Typical olefin mixtures are as shown in the following table:

TABLE I

| Olefin Mixture | Vinyl Olefin | Vinylidene Olefin | Di-Substituted[1] Internal Olefin |
|---|---|---|---|
| Dodecenes | 89.1% | 7.5% | 3.4% |
| Hexadecenes | 68.4% | 24.0% | 7.6% |
| Octadecenes | 55.8% | 38.3% | 5.9% |

[1]No tri-substituted olefins were detected.

The most preferred embodiment of the invention is a process for isomerizing a mixture of olefins containing about 12-20 carbon atoms consisting mainly of vinyl olefins and vinylidene olefins and a minor amount of internal olefins. The process comprises heating the mixture of olefins in contact with a catalytic amount of an iron carbonyl at a temperature of about 200°-300° C. until a substantial amount of the vinylidene olefins have isomerized to form isomerized internal olefins. The process is characterized in that the isomerized internal olefins formed from the vinylidene olefins are mainly di-substituted internal olefins containing 12-20 carbon atoms having the structure:

$$X-CH=CH-Y$$

and only a minor amount of tri-substituted internal olefins having the structure:

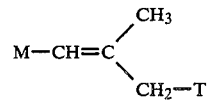

wherein X, Y, M and T are aliphatic hydrocarbon groups such that X plus Y contain about 10-18 carbon atoms and M plus T contain about 8-16 carbon atoms.

The initial mixture of olefins contains about 50-95 wt% vinyl olefin and 5-50 wt% vinylidene olefins. The resultant isomerized product is a mixture of internal olefins which may contain a minor amount, up to about 5%, of non-isomerized vinyl olefin, and none or only small amounts, generally up to about 7 wt%, or tri-substituted olefins. When the amount of vinylidene olefin in the initial feed is less than about 10 wt%, only trace amounts of tri-substituted olefins have been found in the isomerized product. When the amount of vinylidene olefin in the initial olefin feed exceeds about 37 wt%, amounts of tri-substituted olefin up to about 14 wt% but generally in the range of 1-3 wt% have been found in the isomerized product.

The isomerization can be conducted by placing the olefin feed in a pressure reaction vessel and adding a small amount of an iron carbonyl catalyst and heating the mixture, preferably under an inert atmosphere such as nitrogen, to an isomerization temperature. Alternatively, the olefin feed containing a catalytic amount of an iron carbonyl can be passed through a continuous reactor such as a tubular reactor maintained at isomerization temperature. No additional stimuli such as ultraviolet light or ultrasonic energy is needed to activate the iron carbonyl catalyst.

Any iron carbonyl catalyst can be used such as $Fe(CO)_5$, $Fe_2(CO)_9$, $Fe_3(CO)_{12}$ and the like. In the examples, the catalyst added to the olefin mixture was $Fe(CO)_5$.

Only a catalytic amount of the iron carbonyl is needed. A useful range is about 0.01-3.0 wt%. A preferred range is about 0.02-1.0 wt%.

Excellent results have been achieved using 0.04-0.07 wt% iron carbonyl.

The olefin containing the iron carbonyl catalyst is heated to isomerization temperatures. This is a temperature high enough to cause the isomerization reaction to proceed but not so high as to cause excessive decomposition of the olefins. A useful temperature range in which to experiment is about 150°-400° C. A more preferred temperature range is about 150°-350° C. A highly preferred isomerization temperature is about 200°-300° C. Excellent results have been achieved at 220°-280° C.

The isomerization is conducted in the liquid phase so the pressure will at least be the vapor pressure of the olefin mixture at isomerization temperature. Higher pressures can be used by pressurizing with an inert gas such as nitrogen but there is no advantage in this.

The following examples serve to show how the isomerization can be carried out and typical results. In each of the experiments the olefin to be isomerized was placed in an autoclave which was purged with nitrogen. The autoclave was sealed and the olefin mixture was heated to 220°-230° C. Then 0.04-0.07 wt% iron carbonyl was injected into the autoclave. The olefin mixture was maintained at 220°-230° C. for about 20 minutes and then heated to about 260°14 280° C. over a 30 minute period. Isomerization was continued at 260°-280° C. for an additional 30 minutes. The autoclave was then cooled and discharged.

Initial olefin mixtures used in the examples are described in the following table.

TABLE II

| Olefin Type | Composition (wt %) | | |
|---|---|---|---|
| | Examples 1-4 Dodecenes 97 wt % | Examples 5-11 Hexadecenes 97 wt % | Examples 12-15 Hexadecene 20% Octadecene 80% |
| Vinyl | 89.1 | 68.4 | 55.8 |
| Vinylidene | 7.5 | 24.0 | 38.3 |
| Internal[1] | 3.4 | 7.6 | 5.9 |
| Tri-substituted | none | none | none |

[1]Di-substituted

The following table shows the composition of the olefin mixture as analyzed by a Varian EM 390 90 MHz NMR instrument after completion of the isomerization reaction.

TABLE II

| Example | Vinyl Olefin | Internal[3] Olefin | Tri-substituted Olefin | Vinylidene Olefin |
|---|---|---|---|---|
| 1 | 3.6% | 92.2% | ND[1] | 4.2% |
| 2 | 3.5 | 93.5 | ND | 3.0 |
| 3 | 2.9 | 94.3 | ND | 2.8 |
| 4 | 3.4 | 93.6 | ND | 3.0 |
| 5 | 2.1 | 86.4 | ND | 11.5 |
| 6 | 2.7 | 86.7 | ND | 10.6 |
| 7 | 3.2 | 86.6 | ND | 10.0 |
| 8 | 1.2 | 89.3 | 2.1 | 7.4 |
| 9 | 2.6 | 88.5 | ND | 8.0 |

TABLE II-continued

| Example | Vinyl Olefin | Internal[3] Olefin | Tri-substituted Olefin | Vinylidene Olefin |
|---|---|---|---|---|
| 10 | 2.2 | 87.3 | 0.6 | 9.8 |
| 11[2] | 2.3 | 82.2 | ND | 15.5 |
| 12 | 1.7 | 78.2 | 2.3 | 17.8 |
| 13 | 1.6 | 72.9 | 5.1 | 15.5 |
| 14 | 1.1 | 81.4 | 3.5 | 13.9 |
| 15 | 1.5 | 79.5 | 2.8 | 16.2 |

[1]ND, none detected
[2]Isomerized at 220° C. - 3 hours
[3]Di-substituted olefins These results clearly demonstrate that the present process is very effective in isomerizing all olefins and that the vinylidene olefin content of mixtures containing vinylidene olefins form predominantly internal olefins which are not the expected tri-substituted olefins but rather are mainly what is defined herein as di-substituted olefins.

Analysis of the above isomerized olefin mixtures using a Nicolet 360 MHz NMR instrument indicated a somewhat higher content of tri-substituted olefins in the mixture. Specifically analysis of a composite of four individual isomerization products showed the following composition:

| Vinyl olefin | 1.0% |
|---|---|
| Vinylidene | 15.3% |
| Di-substituted | 76.9% |
| Tri-substituted | 6.3% |

It was felt that the analysis at 360 MHz was more sensitive in detecting small amounts of tri-substituted olefins in the presence of large amounts of di-substituted olefins than the results at 90 MHz. Therefore a series of experiments was conducted isomerizing a mixture of $C_{18}$ olefins using an iron carbonyl catalyst and analyzing the product on the Nicolet 360 MHz NMR instrument. The initial olefin mixture used in these experiments was as follows:

| Vinyl olefins | 56.8% |
|---|---|
| Vinylidene olefins | 37.3% |
| Di-substituted | 5.8% |
| Tri-substituted | None detected |

The isomerization conditions were as follows:

| Run No. | |
|---|---|
| 1 | Monel autoclave, 210° C., 30 min. |
| 2 | Monel autoclave, 210° C. 30 min., 240° C. 90 min. |
| 3 | Glass pressure vessel, 220° C. 30 min., 250° C. 45 min. |
| 4 | Monel autoclave, Fe powder, 220° C. 30 min., 245° C. 90 min. |
| 5 | Open system under Argon, 220° C. 80 min., 270° C. 30 min. |

The isomerization products were found (360 MHz NMR) to contain:

TABLE III

| Run No. | Vinyl | Vinylidene | Di-Substituted | Tri-Substituted |
|---|---|---|---|---|
| 1 | 7.3 | 33.0 | 58.4 | 1.4 |
| 2 | 2.1 | 26.1 | 69.1 | 2.7 |
| 3 | 1.1 | 27.6 | 68.9 | 2.4 |
| 4 | 1.7 | 28.0 | 67.6 | 2.7 |

TABLE III-continued

| Run No. | Vinyl | Vinylidene | Di-Substituted | Tri-Substituted |
|---------|-------|------------|----------------|-----------------|
| 5 | 1.8 | 2.0 | 81.9 | 14.3 |

The results showed that whether the vessel was Monel, glass or iron did not make much difference. Temperature and reaction time had an affect on the percent of vinylidene olefins that were isomerized but not much affect on the ratio of di-substituted/tri-substituted olefin that formed from the portion of the vinylidene olefins that was isomerized. This is shown in the following Table IV.

TABLE IV

| Run No. | Percent of Vinylidene Isomerized[1] | % Di-Substituted % Tri-substituted[2] |
|---------|------------------------------------|---------------------------------------|
| 1 | 12 | 69/31 |
| 2 | 30 | 76/24 |
| 3 | 26 | 75/25 |
| 4 | 25 | 71/29 |
| 5 | 95 | 60/40 |

[1] Based on the total vinylidene in initial olefin mixture.
[2] Based on isomerized portion of vinylidene olefins.

These results show that generally 25-30% of the vinylidene olefins in the mixture were isomerized by iron carbonyl and that of this isomerized portion the ratio of % di-substituted/% tri-substituted was about 75/25. This serves to confirm that the major isomerization products from the vinylidene olefins are di-substituted olefins and only a minor amount is tri-substituted or tert-olefin.

I claim:

1. A process for isomerizing the olefinic double bond of a vinylidene olefin containing about 12-20 carbon atoms and having the structure:

$$R'-CH_2-CH_2-(CH_2)_n-\underset{\underset{R''}{|}}{C}=CH_2$$

wherein R' and R" are aliphatic hydrocarbon groups and n is an integer from 0-10, said process comprising contacting said vinylidene olefin with a catalytic amount of an iron carbonyl at a temperature of about 150°-350° C. whereby the major isomerization product of said vinylidene olefin is a di-substituted internal olefin having the structure:

$$R'''-CH=CH-(CH_2)_n-\underset{\underset{R''}{|}}{C}-CH_3$$

wherein R''' and R" are aliphatic hydrocarbon groups and n is an integer from 0-10 and only a minor amount of tri-substituted internal olefin.

2. A process of claim 1 wherein R' and R" contain about 1-20 carbon atoms such that the total number of carbon atoms in said vinylidene olefin is about 12-20.

3. A process of claim 2 wherein R' is a substantially linear aliphatic hydrocarbon group.

4. A process of claim 1 wherein said temperature is about 200°-300° C.

5. A process for isomerizing a mixture of olefins containing about 12-20 carbon atoms, said mixture of olefins consisting essentially of 50 to 95 wt% of vinyl olefins and 5 to 50 wt% of vinylidene olefins and a minor amount of internal olefins, said process comprising heating said mixture of olefins in contact with a catalytic amount of an iron carbonyl at a temperature of about 200°-300° C. until a substantial amount of said vinylidene olefins have isomerized to form isomerized internal olefins, said process being characterized in that said isomerized internal olefins which are formed from said vinylidene olefins are mainly di-substituted internal olefins containing 12-20 carbon atoms and have the structure:

$$X-CH=CH-Y$$

and only a minor amount of tri-substituted internal olefins having the structure:

$$M-CH=C\begin{matrix}CH_3\\ \\CH_2-T\end{matrix}$$

wherein X, Y, M and T are aliphatic hydrocarbon groups such that X plus Y contain about 10-18 carbon atoms and M plus T contain about 8-16 carbon atoms.

6. A process of claim 5 further characterized in that at least 70 wt% of the vinylidene olefins in said mixture of olefins that are isomerized form di-substituted olefins.

* * * * *

UNITED STATES PATENT AND TRADEMARK OFFICE
CERTIFICATE OF CORRECTION

PATENT NO. : 4,587,374

DATED : MAY 6, 1986

INVENTOR(S) : BRUCE C. PETERS

It is certified that error appears in the above-identified patent and that said Letters Patent is hereby corrected as shown below:

Column 3, line 60, reads "quire" and should read -- quite --.

Column 5, line 36, reads "260°14 280°C" and should read -- 260°-280°C --.

Signed and Sealed this

Twelfth Day of August 1986

[SEAL]

Attest:

DONALD J. QUIGG

Attesting Officer

Commissioner of Patents and Trademarks